United States Patent [19]

Effing et al.

[11] Patent Number: 5,702,720
[45] Date of Patent: Dec. 30, 1997

[54] TRANSDERMAL DEVICE FOR THE DELIVERY OF FLURBIPROFEN

[75] Inventors: Jochem Effing, Borken; Eberhard Gruhlke, Ochtrup, both of Germany; Kristin Godbey, Vadnais Heights, Minn.; Wolfgang Welsing, Borken, Germany

[73] Assignee: Minnesota Mining and Manufacturing Company, St. Paul, Minn.

[21] Appl. No.: 577,482

[22] Filed: Dec. 22, 1995

[51] Int. Cl.$^6$ ........................................ A61F 13/02
[52] U.S. Cl. ............................... 424/448; 424/449
[58] Field of Search ................................ 424/448, 449

[56] References Cited

U.S. PATENT DOCUMENTS

| Re. 24,906 | 12/1960 | Ulrich | 206/59 |
|---|---|---|---|
| 3,949,128 | 4/1976 | Ostermeier | 428/152 |
| 4,185,100 | 1/1980 | Rovee et al. | 424/240 |
| 4,393,076 | 7/1983 | Noda et al. | 424/317 |
| 4,473,584 | 9/1984 | Heckler | 424/317 |
| 4,477,468 | 10/1984 | Heckler | 424/317 |
| 4,533,546 | 8/1985 | Kishi et al. | 424/81 |
| 4,701,470 | 10/1987 | Heckler | 514/570 |
| 4,704,406 | 11/1987 | Stanislaus et al. | 514/570 |
| 4,751,087 | 6/1988 | Wick | 424/449 |
| 4,849,418 | 7/1989 | Lohner et al. | 514/163 |
| 5,093,133 | 3/1992 | Wisniewski et al. | 424/484 |
| 5,206,029 | 4/1993 | Brune et al. | 424/489 |
| 5,230,701 | 7/1993 | Meyer et al. | 602/76 |
| 5,266,723 | 11/1993 | Hanna et al. | 562/490 |
| 5,478,567 | 12/1995 | Nakagawa et al. | 524/449 |

FOREIGN PATENT DOCUMENTS

| 0091964-A1 | 10/1983 | European Pat. Off. . |
| 0279519-A1 | 8/1988 | European Pat. Off. . |
| 0338291-A1 | 10/1989 | European Pat. Off. . |
| 0513832-A1 | 11/1992 | European Pat. Off. . |
| 2698787 | 6/1994 | France . |
| 55-139313 | 10/1980 | Japan . |
| 4[1991]99719 | 3/1992 | Japan . |
| 86/02264 | 4/1986 | WIPO . |
| 91/06295 | 5/1991 | WIPO . |
| 91/17740 | 11/1991 | WIPO . |
| 93/08795 | 5/1993 | WIPO . |
| 94/23713 | 10/1994 | WIPO . |
| 95/18603 | 7/1995 | WIPO . |

*Primary Examiner*—D. Gabrielle Phelan
*Attorney, Agent, or Firm*—Gary L. Griswold; Walter N. Kirn; Ted K. Ringsred

[57] ABSTRACT

A transdermal drug delivery device involving an acrylate or methacrylate based copolymer, a skin penetration enhancer, a polyvinylpyrrolidone polymer, and a therapeutically effective amount of flurbiprofen.

18 Claims, No Drawings

TRANSDERMAL DEVICE FOR THE DELIVERY OF FLURBIPROFEN

BACKGROUND OF THE INVENTION

1. Field of the Invention

This invention relates to transdermal drug delivery devices. In another aspect this invention relates to pharmaceutical formulations containing flurbiprofen.

2. Description of the Related Art

Transdermal drug delivery devices are designed to deliver a therapeutically effective mount of drug across the skin of a patient. Transdermal drug delivery devices typically involve a carrier (such as a liquid, gel, or solid matrix, or a pressure sensitive adhesive) into which the drug to be delivered is incorporated. Devices known to the art include reservoir type devices involving membranes that control the rate of drug release to the skin and devices involving a dispersion of the drug in a matrix such as a pressure sensitive adhesive. The skin, however, presents a substantial barrier to ingress of foreign substances into the body. It is therefore often desirable or necessary to incorporate certain materials that enhance the rate at which the drug passes through the skin. However, the type of device, suitable components for use in the device, the transdermal flux rate that is suitable, and the suitable formulation components are dependent upon the particular drug to be delivered.

Flurbiprofen, (±)-2-fluoro-α-methyl[1,1'-biphenyl]-4-acetic acid, is a nonsteroidal antiinflammatory agent which has shown antiinflammatory, analgesic, and antipyretic properties in pharmacologic studies.

SUMMARY OF THE INVENTION

Briefly, in one aspect, this invention provides a transdermal delivery device comprising:

(A) a backing;

(B) an adhesive layer adhered to one surface of the backing and comprising a mixture of (1) a copolymer comprising interpolymerized units derived from
   (a) one or more A monomers selected from the group consisting of alkyl acrylates containing 4 to 10 carbon atoms in the alkyl group and alkyl methacrylates containing 4 to 10 carbon atoms in the alkyl group; and
   (b) one or more ethylenically unsaturated B monomers comprising a functional group selected from the group consisting of carboxylic acid, sulfonamide, urea, carbamate, carboxamide, hydroxy, amino, oxy, oxo and cyano;

(2) flurbiprofen in a therapeutically effective amount;

(3) isopropyl myristate in an amount of about 20 to about 40 percent by weight based on the total weight of the adhesive layer; and (4) polyvinylpyrrolidone in an amount of about 1 to about 10 percent by weight based on the total weight of the adhesive layer, wherein the backing and adhesive layer together has a moisture vapor transmission rate greater than 400 g/m$^2$/24 hr. Preferably the adhesive layer mixture is homogeneous.

DETAILED DESCRIPTION OF THE INVENTION

This invention provides transdermal delivery devices containing flurbiprofen, especially S(+)-flurbiprofen. The flurbiprofen is present in a therapeutically effective amount, i.e., an amount effective to bring about a desired therapeutic result in the treatment of a condition. The amount that constitutes a therapeutically effective amount varies according to the condition being treated, any drugs being coadministered with flurbiprofen, desired duration of treatment, the surface area of the skin over which the device is to be placed, and other components of the transdermal delivery device. Accordingly it is not practical to enumerate particular preferred amounts but such can be readily determined by those skilled in the art with due consideration of these factors. Generally, however, flurbiprofen is present in a device of the invention in an amount by weight of about 1 to about 25 percent, preferably about 5 to 15 percent, by weight based on the total weight of the adhesive layer. In a preferred embodiment the adhesive layer is substantially free of solid undissolved flurbiprofen.

The adhesive layer comprises isopropyl myristate in an mount by weight of about 20 to 40 percent, preferably 25 to 35 percent, based on the total weight of the adhesive layer. The isopropyl myristate generally is dispersed or preferably dissolved in the adhesive layer and enhances flurbiprofen penetration through the skin when this phenomenon is measured using the skin penetration test method described below.

The copolymer used in the practice of the invention preferably is substantially chemically inert to both flurbiprofen and to isopropyl myristate. The inherent viscosity of the copolymer is such as to ultimately provide a suitable pressure sensitive adhesive when used in a device of the invention. Preferably the copolymer has an inherent viscosity in the range 0.2 dl/g to about 2 dl/g, more preferably 0.3 dl/g to about 1.4 dl/g.

Suitable copolymers for use in the adhesive layer preferably comprise about 80 to 95 percent by weight, more preferably 84 to 94 percent by weight, based on the total weight of the copolymer, of interpolymerized units derived from one or more A monomers selected from the group consisting of alkyl acrylates containing 4 to 10 carbon atoms in the alkyl group and alkyl methacrylates containing 4 to 10 carbon atoms in the alkyl group. Examples of suitable alkyl acrylates and methacrylates are n-butyl, n-pentyl, n-hexyl, cyclohexyl, isoheptyl, n-nonyl, n-decyl, isohexyl, isobornyl, 2-ethyloctyl, isooctyl, and 2-ethylhexyl acrylates and methacrylates. Preferred alkyl acrylates include isooctyl acrylate, 2-ethylhexyl acrylate, n-butyl acrylate and cyclohexyl acrylate. A particularly preferred alkyl acrylate is isooctyl acrylate. Particularly preferred alkyl methacrylates include butyl methacrylate, cyclohexyl methacrylate, and isobornyl methacrylate.

The copolymer component of the adhesive layer further comprises interpolymerized units derived from one or more ethylenically unsaturated B monomers, preferably in a total amount from about 5 to 20 percent by weight, more preferably 6 to 16 percent by weight, based on the total weight of the copolymer. Suitable B monomers include those comprising a functional group selected from the group consisting of carboxylic add, sulfonamide, urea, carbamate, carboxamide, hydroxy, amino, oxy, oxo, and cyano. Exemplary B monomers include acrylic acid, methacrylic acid, maleic acid, a hydroxyalkyl acrylate containing 2 to 4 carbon atoms in the hydroxyalkyl group, a hydroxyalkyl methacrylate containing 2 to 4 carbon atoms in the hydroxyalkyl group, acrylamide, methacrylamide, an alkyl substituted acrylamide containing 1 to 8 carbon atoms in the alkyl group, N-vinyl-N-methyl acetamide, N-vinyl valerolactam, N-vinyl caprolactam, N-vinyl-2-pyrrolidone, glycidyl methacrylate, vinyl acetate, alkoxyethyl acrylate containing 1 to 4 carbon atoms in the alkoxy group, alkoxyethyl methacrylate containing 1 to 4 carbon atoms in the alkoxy group, 2-ethoxyethoxyethyl acrylate, furfuryl acrylate, furfuryl methacrylate, tetrahydrofurfuryl acrylate, tetrahydrofurfuryl methacrylate, propylene glycol monomethacrylate, propylene oxide methyl ether acrylate, di(lower)alkylamino ethyl acrylate, di(lower)alkylamino ethyl methacrylate, di(lower alkyl)aminopropyl methacrylamide, acrylonitrile, and methacrylonitrile. Preferred B monomers include N,N-dimethylacrylamide, acrylamide and acrylic acid.

The above described copolymers are known, and methods of preparation are well known to those skilled in the art, having been described for example in U.S. Pat. RE 24,906 (Ulrich), the disclosure of which is incorporated herein by reference.

The adhesive layer further comprises polyvinylpyrrolidone (PVP). The term "polyvinylpyrrolidone" means either a homopolymer of N-vinyl-2-pyrrolidone or a copolymer comprising interpolymerized units derived from N-vinyl-2-pyrrolidone and these units are present in an amount by weight of more than 50 percent based on the total weight of the copolymer. Examples of suitable PVP homopolymers and copolymers are those meeting the specifications set forth in the European Pharmacopoeia monographs for "polyvidone" and "copolyvidonum". Such polyvinylpyrrolidones are available under the tradename KOLLIDON from BASF Aktiengesellschaft. Preferred PVP homopolymers are Kollidon 25, Kollidon 30 and Kollidon 90. A preferred PVP copolymer is Kollidon VA 64 which is a copolymer of N-vinyl-2-pyrrolidone and vinyl acetate. The polyvinylpyrrolidone is present in the adhesive layer in an amount by weight of about 1 to 10 percent, more preferably 3 to 8 percent by weight, based on the total weight of the adhesive layer. The incorporation of the PVP into the adhesive layer serves to lower the tack and to increase the cohesive strength of the adhesive layer. If the tack is too high, removal of the device from skin can be painful. If the cohesive strength is too low, then an unacceptable amount of adhesive residue may be left on the skin when the device is removed.

The flurbiprofen containing transdermal delivery device of the invention also comprises a backing. The backing is flexible such that the device conforms to the skin. The backing is nonocclusive such that a transdermal delivery device of the invention has a moisture vapor transmission rate greater than 400 g/m$^2$/24 hr when this phenomenon is measured using the test method described below. Examples of suitable backing materials include nonwoven webs and perforated films. The backing should be substantially inert to the ingredients of the adhesive layer.

A particularly preferred backing comprises a nonwoven polypropylene web having multidirectional stretch. Such webs are known and can be prepared by methods known to those skilled in the art and described for example, in U.S. Pat. No. 3,949,128 (Ostermeier), the disclosure of which is incorporated herein by reference. Briefly stated, a suitably bonded (e.g., thermally spot welded or spunbonded) nonwoven polypropylene web is stretched in the machine direction while being heated (130°–150° C.) to provide a web that has stretch in the cross direction. The web is then imparted with stretch in the machine direction by creping using readily available equipment, e.g., a MICROCREPER™ (available from MICREX Corp.). The resulting webs provide a soft, conformable, stretchable, breathable backing. They are resistant to certain fatty acid ester skin penetration enhancers including isopropyl myristate. The webs may optionally be further treated (e.g., calendering to provide a smoother surface for lamination of the drug-in-adhesive matrix or corona treatment to enhance the bonding of the drug-in-adhesive matrix to the web.)

The moisture vapor transmission rate (MVTR) of living skin has been estimated to be about 400 g/m$^2$/24 hr (Kuno, Yas in "Human Perspiration", Charles G. Thomas, Springfield, Ill., USA, 1956, pp 26–27). Devices that have a MVTR substantially below this value are generally described as occlusive. The flurbiprofen containing transdermal delivery devices of the invention are nonocclusive and have a (MVTR) greater than 400 g/m$^2$/24 hr when this phenomenon is measured using the test method described below. This property results in a reduction of moisture buildup on the skin beneath the device and to a corresponding reduction in the amount of skin maceration that occurs.

The flurbiprofen containing transdermal delivery devices of the invention can be prepared by combining a solution containing the copolymer, the isopropyl myristate, and the flurbiprofen in an organic solvent (e.g., ethyl acetate) with a solution containing polyvinylpyrrolidone in an organic solvent (e.g., isopropanol) to afford a coating formulation. The coating formulation is coated using conventional methods onto a suitable release liner to provide a predetermined uniform thickness of the coating formulation. Suitable release liners include conventional release liners comprising a known sheet material such as a polyester web, polyolefin web, or a polystyrene web, or a polyethylene-coated paper coated with a suitable fluoropolymer or silicone based coating. The coated release liner is oven dried and then laminated onto a backing material using conventional methods.

The flurbiprofen containing transdermal delivery devices of the invention can be made in the form of an article such as a tape, a patch, a sheet, a dressing or any other form known to those skilled in the art. Generally the device will be in the form of a patch of a size suitable to deliver a preselected amount of flurbiprofen through the skin. Generally the device will have a surface area of about 50 cm$^2$ to about 200 cm$^2$.

A flurbiprofen containing device of the invention can be used to treat any condition capable of treatment with flurbiprofen, e.g., pain and inflammation associated with arthritis and soft tissue injury. The device can be placed on the skin and allowed to remain for a time sufficient to achieve or maintain the intended therapeutic effect. The time that constitutes a sufficient time can be selected by those skilled in the art with consideration of the flux rate of the device of the invention and upon the condition being treated.

The examples set forth below are intended to illustrate the invention.

In Vitro Skin Penetration Test Method

The skin penetration data given in the examples below was obtained using the following test method. A diffusion cell is used. Hairless mouse skin (female hairless mice, 3–4 weeks old) or human cadaver skin is used. The skin is mounted epidermal side up between the upper and the lower portion of the cell, which are held together by means of a ball joint clamp.

The portion of the cell below the mounted skin is completely filled with receptor fluid ("HEPES" (N-[2-hydroxyethyl]piperazine-N'-[2-ethanesulfonic acid]) buffered Hanks balanced salt solution, pH 7.2, supplemented with 1.5 mmolar sodium azide) such that the receptor fluid is in contact with the skin. The receptor fluid is stirred using a magnetic stir bar. The sampling port is covered except when in use.

When a transdermal delivery device is evaluated, the skin is placed across the orifice of the lower portion of the diffusion cell, the release liner is removed from a 1.55 cm² patch and the patch is applied to the skin and pressed to cause uniform contact with the skin. The diffusion cell is assembled and the lower portion is filled with receptor fluid.

The cell is then placed in a constant temperature (32°±1.5° C.) and humidity (45±5% relative humidity) chamber. The receptor fluid is stirred by means of a magnetic stirrer throughout the experiment to assure a uniform sample and a reduced diffusion barrier on the dermal side of the skin. The entire volume of receptor fluid is withdrawn at specified time intervals (3, 6, 9, 12, 24, 36 and 48 hours) and immediately replaced with fresh fluid. The withdrawn fluid is analyzed for drug content using reverse phase high performance liquid chromatography. The cumulative amount of S(+)-flurbiprofen penetrating the skin is calculated.

Moisture Vapor Transmission Rate Test Method

The Moisture Vapor Transmission Rate (MVTR) data given in the examples below was obtained using the following test method. This test method is a modified version of ASTM E 96-80.

A sample having a diameter of 31 mm is die cut from the laminate being tested. An adhesive-backed foil ring having an inner diameter ("i.d.") of 24.4 mm and an outer diameter ("o.d.") of 37.5 mm is laminated to the backing surface of the test sample. The release liner is removed from the test sample and a second adhesive-backed foil ring (i.d. 24.4 mm; o.d. 37.5 mm) is laminated to the adhesive surface of the test sample such that the two foil rings are concentrically aligned and the test sample is sandwiched between the adhesive surfaces of the foil rings. The resulting foil/sample/foil laminate is smoothed to remove any wrinkles or voids.

A brown glass jar (100 mL) having a 40 mm diameter opening is half-filled with 50 mL of distilled water. The jar is fitted with a screw-on lid having a 30 mm diameter hole.

The foil/sample/foil laminate is concentrically positioned in the lid such that the adhesive surface of the sample will be facing the interior of the jar when the lid is screwed onto the jar. A gasket having an inner diameter of 30 mm is inserted into the lid and the resulting lid/laminate/gasket sub-assembly is screwed loosely onto the jar.

The assembly is placed into a chamber maintained at a temperature of 40° C. and 20% relative humidity. The assembly is removed from the chamber after 4 hours and weighed to the nearest 0.01 g ($W_1$). The lid is screwed tightly onto the jar and the assembly is returned to the chamber. After 24 hours the assembly is removed from the chamber and weighed to the nearest 0.01 g ($W_2$).

The MVTR of the sample (measured in grams of water transmitted per square meter of sample area over a 24 hour period) may then be calculated according to the following equation:

$$MVTR = \frac{(W_1 - W_2)}{4.676} \times 10000$$

Six (6) samples of each laminate are run and the average of the 6 samples is reported.

180 Degree Peel Adhesion to Stainless Steel

The values given for 180 degree peel adhesion to stainless steel in the examples below were obtained using a modified version of ASTM D 3330-90.

A 2.54 cm by 7.62 cm sample is die cut from the laminate being tested. The release liner is peeled down 1 cm and the exposed adhesive surface is adhered to a leader strip. (If a coated release liner is being used as a leader then the adhesive surface should be attached to the uncoated side.) The release liner is removed from the test sample. The test sample is positioned adhesive side down, lengthwise with and approximately in the center of the stainless steel test surface (a 5 cm by 14 cm stainless steel plate that has been washed once with 4-hydroxy-4-methyl-2-pentanone and three times with acetone or ethyl acetate). The sample is rolled down using one forward and one reverse pass with a 2 Kg roller moved at a rate of approximately 6 mm/sec. The sample is then allowed to stand at ambient temperature for 15 minutes. The peel force required to remove the tape at 180 degree angle is measured using an appropriate piece of test equipment (e.g., Frank Universalprüfmaschine 81565 or Instron machine 4201). The rate of removal is 230 mm/min. The force of removal is reported in Newtons. Ten (10) samples of each laminate are run and the average of the 10 samples is reported.

Preparation of Isooctyl Acrylate/Acrylic Acid (90/10) Copolymer

A flask equipped with an agitator, condenser, nitrogen inlet tube and an addition funnel is charged with isooctyl acrylate (72.0 g), acrylic acid (8.0 g) and ethyl acetate (78.1 g). The mixture is heated to 60° C. with medium agitation and purged with nitrogen to remove oxygen. Lucidol 75 (0.07 g, available from Elf Atochem North America) premixed in ethyl acetate (3.0 g) is added to initiate reaction. The reaction temperature is maintained at 60° C. Ethyl acetate (1.5 g) is added to the polymer solution every 30 minutes until the conversion of isooctyl acrylate to polymer reaches a minimum of 95%, typically 20–30 hours. An additional charge of Lucidol 75 (0.07 g) premixed with ethyl acetate (3.0 g) is added after 5 hours and nine hours reaction time. When 95% minimum reaction conversion is achieved, the resulting polymer solution is diluted with heptane to 20–23% solids, cooled and drained. The inherent viscosity in ethyl acetate at 0.15 g./dl is measured at 1.7–2.0 dl/g. The inherent viscosity is measured by conventional means using a Canon-Fenske #50 viscometer in a water bath controlled at 27° C. to measure the flow time of 10 milliliters of the polymer solution. The test procedure and apparatus are described in detail in "Textbook of Polymer Science", F. W. Billmeyer, Wiley Interscience, Second Edition, 1971, pages 84 and 85.

Preparation of "Dried" Adhesive

Dried adhesive is prepared by coating a solution of the adhesive copolymer at a thickness of 500 μm onto a release liner. The coated release liner is oven dried to remove solvent and reduce the amount of residual monomers. The dried adhesive is stripped off the release liner and stored in a container.

Preparation of Multidirectional Stretch Polypropylene Backing

A spunbonded polypropylene nonwoven web with an offset intermittent spot welded structure and a basis weight of a nominal 60 grams per square meter (available as LUTRASIL® LS-4160 from Freudenberg Spunweb Co.) was heated (about 138° C.) and stretched under tension (accomplished by adjusting the unwind and wind-up tensions or speeds to produce a 1:1.5 (±0.1) differential) using conventional equipment in a process known as "necking down" or "stretch-setting". This process reduces the width of the web, increases the length of the web and imparts a stretch in the cross-web direction. The "necked down" web was then microcreped using a MICROCREPER™ (available from the MICREX Corp., Walpole, Mass., USA) with compression ratios from 30% to 40% and a temperature set at 70° C. This process imparts a stretch in the down-web or machine direction. The resulting multidirectional stretch web was calendared on conventional equipment at a temperature of about 138° C. and a pressure of 100 psi (7.0 Kg/cm$^2$) using a small (about 1.5 mm$^2$) waffle patterb top roll and a smooth chrome bottom roll to produce a smoother surface for lamination of the drug-in-adhesive matrix while retaining the multidirectional stretch properties.

EXAMPLE 1

A solution of polyvinylpyrrolidone (4.69 g of Kollidon 30) in isopropanol (166.7 g) was added to a solution containing isopropyl myristate (57.14 g), S(+)-flurbiprofen (13.3 g), and adhesive (120 g of dried 90/10 isooctyl acrylate/acrylic acid copolymer) in ethyl acetate (480 g) to afford a homogeneous coating formulation. The formulation was knife coated at a wet thickness of 650 μm onto a release liner (3M Scotchpak™ 1022 Release Liner). The coated release liner was oven dried for 10 min with the following temperature program: first heating zone at 65° C., second heating zone at 75° C., and third heating zone at 90° C. The polypropylene backing prepared above was corona treated then laminated to the coated liner. The resulting laminate had a drug loading of 0.63 mg/cm$^2$. The laminate was die cut into 1.55 cm$^2$ patches. Penetration through hairless mouse skin was determined using the test method described above. The results are shown in Table 1 below where each value is the average of six independent determinations. An identical sized sample of a commercially available flurbiprofen device (ADOFEED, Mikasa) was also tested.

EXAMPLE 2

A solution of vinylpyrrolidone-vinyl acetate copolymer (6.91 g of Kollidon VA 64) in isopropanol (66.7 g) was added to a solution containing isopropyl myristate (57.14 g), S(+)-flurbiprofen (13.3 g), and adhesive (120 g of dried 90/10 isooctyl acrylate/acrylic acid copolymer) in ethyl acetate (480 g) to afford a homogeneous coating formulation. The formulation was knife coated at a wet thickness of 650 μm onto a release liner (3M Scotchpak™ 1022 Release Liner). The coated release liner was oven dried for 10 min with the following temperature program: first heating zone at 65° C., second heating zone at 75° C., and third heating zone at 90° C. The polypropylene backing prepared above was corona treated then laminated to the coated liner. The resulting laminate had a drag loading of 0.82 mg/cm$^2$. The laminate was die cut into 1.55 cm$^2$ patches. Penetration through hairless mouse skin was determined using the test method described above. The results are shown in Table 1 below where each value is the average of six independent determinations.

EXAMPLE 3

A solution of vinylpyrrolidone-vinyl acetate copolymer (7.94 g of Kollidon VA 64) in isopropanol (66.7 g) was added to a solution containing isopropyl myristate (57.14 g), S(+)-flurbiprofen (13.3 g), and adhesive (120 g of dried 90/10 isooctyl acrylate/acrylic acid copolymer) in ethyl acetate (480 g) to afford a homogeneous coating formulation. The formulation was knife coated at a wet thickness of 650 μm onto a release liner (3M Scotchpak™ 1022 Release Liner). The coated release liner was oven dried for 10 min with the following temperature program: first heating zone at 65° C., second heating zone at 75° C., and third heating zone at 90° C. The polypropylene backing prepared above was corona treated then laminated to the coated liner. The resulting laminate had a drug loading of 0.88 mg/cm$^2$. The laminate was die cut into 1.55 cm$^2$ patches. Penetration through hairless mouse skin was determined using the test method described above. The results are shown in Table 1 below where each value is the average of six independent determinations.

EXAMPLE 4

A solution of vinylpyrrolidone-vinyl acetate copolymer (10.52 g of Kollidon VA 64) in isopropanol (183.3 g) was added to a solution containing isopropyl myristate (57.4 g), S(+)-flurbiprofen (13.39 g), and adhesive (110 g of dried 90/10 isooctyl acrylate/acrylic acid copolymer) in a mixture of ethyl acetate (352 g) and isopropanol (88 g) to afford a homogeneous coating formulation. The formulation was knife coated onto a release liner (3M Scotchpak™ 1022 Release Liner). The coated release liner was oven dried for 10 min with the following temperature program: first heating zone at 65° C., second heating zone at 75° C., and third heating zone at 90° C. The coated liner was then laminated to the polypropylene backing prepared above. The resulting laminate had a drug loading of 0.7 mg/cm$^2$. The laminate was die cut into 1.55 cm$^2$ patches. Penetration through hairless mouse skin was determined using the test method described above. The results are shown in Table 1 below where each value is the average of six independent determinations.

EXAMPLE 5

A solution of vinylpyrrolidone-vinyl acetate copolymer (13.75 g of Kollidon VA 64) in isopropanol (183.3 g) was added to a solution containing isopropyl myristate (58.9 g), S(+)-flurbiprofen (13.75 g), and adhesive (110 g of dried 90/10 isooctyl acrylate/acrylic acid copolymer) in a mixture of ethyl acetate (352 g) and isopropanol (88 g) to afford a homogeneous coating formulation. The formulation was knife coated onto a release liner (3M Scotchpak™ 1022 Release Liner). The coated release finer was oven dried for 10 min with the following temperature program: first heating zone at 65° C., second heating zone at 75° C., and third heating zone at 90° C. The coated finer was then laminated to the polyropylene backing prepared above. The resulting laminate had a drug loading of 0.7 mg/cm$^2$. The laminate was die cut into 1.55 cm$^2$ patches. Penetration through hairless mouse skin was determined using the test method described above. The results are shown in Table 1 below where each value is the average of six independent determinations.

EXAMPLE 6

A solution of vinylpyrrolidone-vinyl acetate copolymer (5.3 g of Kollidon VA 64) in isopropanol (175 g) was added to a solution containing isopropyl myristate (57.4 g), S(+)-flurbiprofen (16.28 g), and adhesive (105 g of dried 90/10 isooctyl acrylate/acrylic acid copolymer) in a mixture of ethyl acetate (336 g) and isopropanol (84 g) to afford a homogeneous coating formulation. The formulation was knife coated onto a release liner (3M Scotchpak™ 1022 Release Liner). The coated release liner was oven dried for 10 min with the following temperature program: first heating zone at 65° C., second heating zone at 75° C., and third heating zone at 90° C. The coated liner was then laminated to the polypropylene backing prepared above. The resulting laminate had a drug loading of 0.7 mg/cm$^2$. The laminate was die cut into 1.55 cm$^2$ patches. Penetration through hairless mouse skin was determined using the test method described above. The results are shown in Table 1 below where each value is the average of six independent determinations.

COMPARATIVE EXAMPLE 1

Isopropyl myristate (239 g), S(+)-flurbiprofen (56 g), and adhesive (503 g of dried 90/10 isooctyl acrylate/acrylic acid copolymer) were dissolved in ethyl acetate (2260 g) afford a homogeneous coating formulation. The formulation was coated through an extrusion die onto a release liner (3M Scotchpak™ 1022 Release Liner). The coated release liner was oven dried for 10 min with the following temperature program: first heating zone at 65° C., second heating zone at 75° C., and third heating zone at 90° C. The coated liner was then laminated to the polypropylene backing prepared above. The resulting laminate had a drug loading of 0.7 mg/cm$^2$ but did not contain PVP. The laminate was die cut into 1.55 cm$^2$ patches. Penetration through hairless mouse skin was determined using the test method described above. The results are shown in Table 1 below (C1) where each value is the average of six independent determinations.

TABLE 1

Hairless Mouse Skin Penetration

| Example Number | Cumulative Amount Penetrating (μg/cm$^2$/24 hr) |
|---|---|
| 1 | 151.8 |
| 2 | 166.9 |
| 3 | 136.3 |
| 4 | 70.9 |
| 5 | 91.1 |
| 6 | 91.6 |
| C1 | 190.8 |
| ADOFEED | 50.2 |

The data in Table 1 show that a device of the invention can have a flux rate that is higher than that of the commercially available product.

EXAMPLE 7

A solution of vinylpyrrolidone-vinyl acetate copolymer (201.34 g of Kollidon VA 64) in isopropanol (2684.1 g) was added to a solution containing isopropyl myristate (862.7 g), S(+)-flurbiprofen (201.28 g), and adhesive (1610.3 g of dried 90/10 isooctyl acrylate/acrylic acid copolymer) in a mixture of ethyl acetate (5155 g) and isopropanol (1288.5 g) to afford a homogeneous coating formulation. The formulation was coated through an extrusion die onto a release liner (3M Scotchpak™ 1022 Release Liner). The coated release liner was oven dried for 10 min with the following temperature program: first heating zone at 65° C., second heating zone at 75° C., and third heating zone at 90° C. The polypropylene backing prepared above was corona treated then laminated to the coated liner. The resulting laminate had a drug loading of 0.7 mg/cm$^2$.

The laminate was die cut into 1.55 cm$^2$ patches. Penetration through hairless mouse skin was determined using the test method described above. The results are shown in Table 2 below where each value is the average of nine independent determinations. Penetration through human cadaver skin was determined using the test method described above. The results are shown in Table 3 below where each value is the average of five independent determinations. An identically sized sample of ADOFEED was also tested.

The tack was measured using ASTM D-2979-71 and found to be 143.60 g/cm$^2$ (average often independent determinations).

The adhesion on steel was measured using the test method described above and found to be 2.33 Newton (average of seven independent determinations).

TABLE 2

Hairless Mouse Skin Penetration

| Example Number | Cumulative Amount Penetrating (μg/cm$^2$) | | |
|---|---|---|---|
| | 12 hour | 24 hour | 48 hour |
| 7 | 73.52 | 151.32 | 290.02 |
| ADOFEED | 24.62 | 52.17 | 93.12 |

TABLE 3

Human Cadaver Skin Penetration

| Example Number | Cumulative Amount Penetrating (μg/cm$^2$) | | |
|---|---|---|---|
| | 12 hour | 24 hour | 48 hour |
| 7 | 32.63 | 63.28 | 112.18 |
| ADOFEED | 11.57 | 32.79 | 67.27 |

The data in Tables 2 and 3 show that a device of the invention can have a flux rate that is higher than that of the commercially available product.

Moisture Vapor Transmission Rate

The moisture vapor transmission rate of the transdermal delivery device prepared in Example 7 was compared with those of the commercially available ADOFEED device and of the device described in Example 1 of WO 94/23713 (indicated as C2 in Table 4). The rates were determined using the test method described above and are summarized in Table 4 below.

TABLE 4

| Moisture Vapor Transmission Rate (g/m$^2$/24 hr) | |
|---|---|
| Example Number | |
| 7 | 442 |
| C2 | 74.8 |
| ADOFEED | 3497 |

The data in Table 4 show that the device of Example 7 is nonocclusive whereas that of C2 is occlusive.

Placebo 1

A placebo (without drug) device was prepared as follows. A solution of vinylpyrrolidone-vinyl acetate copolymer (3.63 g of Kollidon VA 64) in isopropanol (183.25 g) was added to a solution containing isopropyl myristate (54.25 g) and adhesive (110.08 g of dried 90/10 isooctyl acrylate/acrylic acid copolymer) in a mixture of ethyl acetate (352.5 g) and isopropanol (88.69 g) to afford a homogeneous coating formulation. The formulation was knife coated at 600 μM onto a release liner (3M Scotchpak™ 1022 Release Liner). The coated release liner was oven dried for 10 min with the following temperature program: first heating zone at 65° C., second heating zone at 75° C., and third heating zone at 90° C. The polypropylene backing prepared above was corona treated then laminated to the coated liner.

The tack was measured using ASTM D-2979-71 and found to be 201.7 g/cm² (average often independent determinations).

The adhesion on steel was measured using the test method described above and found to be 1.24 Newton (average of six independent determinations).

Placebo 2

A solution of vinylpyrrolidone-vinyl acetate copolymer (5.52 g of Kollidon VA 64) in isopropanol (183.4 g) was added to a solution containing isopropyl myristate (55 g) and adhesive (110.06 g of dried 90/10 isooctyl acrylate/acrylic acid copolymer) in a mixture of ethyl acetate (352 g) and isopropanol (88.25 g) to afford a homogeneous coating formulation. The formulation was knife coated at 600 μM onto a release liner (3M Scotchpak™ 1022 Release Liner). The coated release liner was oven dried for 10 min with the following temperature program: first heating zone at 65° C., second heating zone at 75° C., and third heating zone at 90° C. The polypropylene backing prepared above was corona treated then laminated to the coated liner.

Skin Adhesion

The laminates prepared in Placebo 1, Placebo 2, Comparative Example 1, and Example 7 were cut into strips measuring 1 inch by 3 inches (2.5 cm by 7.6 cm). The release liners were removed. Ten human subjects placed one strip of each laminate (total of four strips) onto the inner forearm for two hours. Each subject rated the adhesion of each laminate using one of six descriptions (very strong, strong, acceptable, comfortable, poor, none). The results are summarized in Table 5 below where all percents are percent by weight of the adhesive layer. The data in Table 5 show that the inclusion of PVP in the adhesive layer reduces the aggressiveness of the adhesive and provides a more comfortable device.

carbon atoms in the alkyl group and alkyl methacrylates coming 4 to 10 carbon atoms in the alkyl group; and (b) one or more ethylenically unsaturated B monomers comprising a functional group selected from the group consisting of carboxylic acid, sulfonamide, urea, carbamate, carboxamide, hydroxy, amino, oxy, oxo and cyano;

(2) flurbiprofen in a therapeutically effective amount;

(3) isopropyl myristate in an amount of about 20 to about 40 percent by weight based on the total weight of the adhesive layer, and (4) a polyvinylpyrrolidone in an amount of about 1 to about 10 percent by weight based on the total weight of the adhesive layer, wherein the device has a moisture vapor transmission rate greater than 400 g/m²/24 hr.

2. A device according to claim 1, wherein the flurbiprofen is present in an amount of about 1 to about 25 percent by weight based on the total weight of the adhesive layer.

3. A device according to claim 1, wherein the flurbiprofen is present in an amount of about 5 to about 15 percent by weight based on the total weight of the adhesive layer.

4. A device according to claim 1, wherein the adhesive layer mixture is homogeneous.

5. A device according to claim 1, wherein the adhesive layer is substantially free of solid undissolved flurbiprofen.

6. A device according to claim 1, wherein the flurbiprofen is S(+)-flurbiprofen.

7. A device according to claim 1, wherein the one or more A monomers are selected from the group consisting of isooctyl acrylate, 2-ethylhexyl acrylate, butyl acrylate, and cyclohexyl acrylate.

8. A device according to claim 1, wherein the A monomer is isooctyl acrylate.

9. A device according to claim 1, wherein the one or more B monomers are selected from the group consisting of acrylic acid, methacrylic acid, acrylamide, methacrylamide, an alkyl substituted acrylamide containing 1 to 4 carbon atoms in the alkyl group, a dialkylacrylamide having 1 or 2 carbon atoms in the alkyl group and a mixture thereof.

10. A device according to claim 1, wherein the B monomer is acrylic acid.

11. A device according to claim 1, wherein the copolymer comprises 80 to 95 percent by weight, based on the total

TABLE 5

| | | | | Adhesion (number of subjects selecting description) | | | | | |
|---|---|---|---|---|---|---|---|---|---|
| Laminate | % Drug | % IPM | % PVP | Very strong | Strong | Acceptable | Comfortable | Poor | None |
| Placebo 1 | 0 | 32.3 | 2.16 | 0 | 1 | 3 | 6 | 0 | 0 |
| Placebo 2 | 0 | 32.2 | 3.2 | 0 | 0 | 4 | 5 | 1 | 0 |
| C1 | 7.0 | 29.95 | 0 | 2 | 7 | 1 | 0 | 0 | 0 |
| Example 7 | 7.0 | 30.0 | 7.0 | 1 | 2 | 5 | 1 | 1 | 0 |

What is claimed is:

1. A transdermal delivery device comprising:

(A) a backing;

(B) an adhesive layer adhered to one surface of the backing and consisting essentially of a mixture of (1) a copolymer comprising interpolymerized units derived from (a) one or more A monomers selected from the group consisting of alkyl acrylates containing 4 to 10 weight of the copolymer, of interpolymerized units derived from said A monomers.

12. A device according to claim 1, wherein the copolymer comprises 5 to 20 percent by weight, based on the total weight of the copolymer, of interpolymerized units derived from said B monomers.

13. A device according to claim 1, wherein the isopropyl myristate is present in an amount of about 25 to 35 percent by weight based on the total weight of the adhesive layer.

14. A device according to claim 1, wherein the polyvinylpyrrolidone is present in an amount of about 3 to 8 percent by weight based on the total weight of the adhesive layer.

15. A device according to claim 1, wherein the polyvinylpyrrolidone is a homopolymer.

16. A device according to claim 1, wherein the polyvinylpyrrolidone is a copolymer of N-vinyl-2-pyrrolidone and vinyl acetate.

17. A device according to claim 1, wherein the backing comprises a nonwoven polypropylene web having multidirectional stretch.

18. A transdermal delivery device comprising:
(A) a backing comprising a nonwoven polypropylene web having multidirectional stretch;
(B) an adhesive layer adhered to one surface of the backing and consisting essentially of a homogeneous mixture of
(1) a copolymer comprising
  (a) about 84 to 94 percent by weight of interpolymerized units derived from alkyl acrylates containing 4 to 10 carbon atoms in the alkyl group, and
  (b) about 6 to 16 percent by weight of interpolymerized units derived from monomers selected from the group consisting of acrylic acid, acrylamide and dimethylacrylamide;
(2) 5 to 15 percent by weight of S(+)-flurbiprofen based on the total weight of the adhesive layer;
(3) isopropyl myristate in an amount of about 25 to about 35 percent by weight based on the total weight of the adhesive layer; and
(4) a polyvinylpyrrolidone in an amount of about 3 to about 8 percent by weight based on the total weight of the adhesive layer, wherein the device has a moisture vapor transmission rate greater than 400 $g/m^2/24$ hr.

* * * * *